US010905875B2

(12) United States Patent
Gross (10) Patent No.: US 10,905,875 B2
(45) Date of Patent: *Feb. 2, 2021

(54) ELECTRICAL TREATMENT OF HYDROCEPHALUS

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 400 days.

This patent is subject to a terminal disclaimer.

(21) Appl. No.: 15/618,325

(22) Filed: Jun. 9, 2017

(65) Prior Publication Data

US 2017/0274207 A1 Sep. 28, 2017

Related U.S. Application Data

(63) Continuation of application No. 13/872,794, filed on Apr. 29, 2013, now Pat. No. 9,731,122.

(51) Int. Cl.
*A61N 1/32* (2006.01)
*A61N 1/36* (2006.01)
*A61N 1/05* (2006.01)
*A61N 1/30* (2006.01)

(52) U.S. Cl.
CPC .......... *A61N 1/327* (2013.01); *A61N 1/0536* (2013.01); *A61N 1/306* (2013.01); *A61N 1/36082* (2013.01); *A61N 1/36139* (2013.01)

(58) Field of Classification Search
CPC .. A61N 1/327; A61N 1/36139; A61N 1/0536; A61N 1/36082; A61N 1/306
See application file for complete search history.

(56) References Cited

U.S. PATENT DOCUMENTS

| 4,044,774 A | 8/1977 | Corbin et al. |
| 4,503,863 A | 3/1985 | Katims |
| 5,088,977 A | 2/1992 | Sibalis |
| 5,121,754 A | 6/1992 | Mullett |

(Continued)

FOREIGN PATENT DOCUMENTS

| JP | 2004321242 A | 11/2004 |
| JP | 2007501067 A | 1/2007 |

(Continued)

OTHER PUBLICATIONS

Sawyer, P N et al. "Measurement of streaming potentials of mammalian blood vessels, aorta and vena cava, in vivo." Biophysical journal vol. 6,5 (1966): 641-51. doi:10.1016/S0006-3495(66)86683-3, https://www.ncbi.nlm.nih.gov/pmc/articles/PMC1368020/, viewed on Jul. 22, 2019.*

(Continued)

*Primary Examiner* — Christopher Koharski
*Assistant Examiner* — James Moss
(74) *Attorney, Agent, or Firm* — Sughrue Mion, PLLC (57) ABSTRACT

A method is provided that includes implanting a first electrode at a first site in a brain of a subject suffering from hydrocephalus, and a second electrode at a second site in the subject. The hydrocephalus is treated by electroosmotically driving fluid out of the first site, by applying a treatment voltage between the first and the second electrodes.

19 Claims, 7 Drawing Sheets

(56) References Cited

U.S. PATENT DOCUMENTS

| | | | |
|---|---|---|---|
| 5,433,739 A | 7/1995 | Sluijter et al. | |
| 5,529,574 A | 6/1996 | Frackelton | |
| 5,792,100 A | 8/1998 | Shantha | |
| 5,911,223 A | 6/1999 | Weaver et al. | |
| 5,938,690 A | 8/1999 | Law et al. | |
| 6,041,252 A | 3/2000 | Walker et al. | |
| 6,146,380 A | 11/2000 | Racz et al. | |
| 6,161,047 A | 12/2000 | King et al. | |
| 6,360,750 B1 | 3/2002 | Gerber et al. | |
| 6,567,702 B1 | 5/2003 | Nekhendzy et al. | |
| 6,591,138 B1 | 7/2003 | Fischell et al. | |
| 6,602,248 B1 | 8/2003 | Sharps et al. | |
| 6,620,155 B2 | 9/2003 | Underwood et al. | |
| 6,941,172 B2 | 9/2005 | Nachum | |
| 6,997,941 B2 | 2/2006 | Sharkey et al. | |
| 7,013,177 B1 | 3/2006 | Whitehurst et al. | |
| 7,120,489 B2 | 10/2006 | Shalev et al. | |
| 7,217,351 B2 | 5/2007 | Krumme | |
| 7,223,227 B2 | 5/2007 | Pflueger | |
| 7,270,659 B2 | 9/2007 | Ricart et al. | |
| 7,317,947 B2 | 1/2008 | Wahlstrand et al. | |
| 7,398,121 B2 | 7/2008 | Matsumura et al. | |
| 7,509,171 B2 | 3/2009 | DiMauro | |
| 7,640,062 B2 | 12/2009 | Shalev | |
| 7,831,306 B2 | 11/2010 | Finch et al. | |
| 7,860,569 B2 | 12/2010 | Solberg et al. | |
| 8,190,248 B2 | 5/2012 | Besio et al. | |
| 8,457,761 B2 | 6/2013 | Wariar | |
| 8,577,469 B2 | 11/2013 | Gross | |
| 8,676,348 B2 | 3/2014 | Gross | |
| 9,616,221 B2 | 4/2017 | Gross | |
| 9,724,513 B2 | 8/2017 | Lane et al. | |
| 9,731,122 B2* | 8/2017 | Gross | A61N 1/327 |
| 10,398,884 B2 | 9/2019 | Lad et al. | |
| 2002/0151948 A1 | 10/2002 | King et al. | |
| 2002/0183683 A1 | 12/2002 | Lerner | |
| 2003/0130707 A1 | 7/2003 | Gan et al. | |
| 2003/0158589 A1 | 8/2003 | Katsnelson | |
| 2003/0216792 A1 | 11/2003 | Levin et al. | |
| 2003/0225331 A1 | 12/2003 | Diederich et al. | |
| 2004/0002746 A1 | 1/2004 | Ryan et al. | |
| 2004/0019381 A1 | 1/2004 | Pflueger | |
| 2004/0049180 A1 | 3/2004 | Sharps et al. | |
| 2004/0116977 A1 | 6/2004 | Finch et al. | |
| 2004/0210209 A1 | 10/2004 | Yeung et al. | |
| 2005/0010205 A1 | 1/2005 | Hovda et al. | |
| 2005/0021104 A1 | 1/2005 | DiLorenzo | |
| 2005/0119650 A1 | 6/2005 | Sanders et al. | |
| 2005/0137646 A1 | 6/2005 | Wallace et al. | |
| 2005/0137647 A1* | 6/2005 | Wallace | A61N 1/0529 607/45 |
| 2005/0159790 A1 | 7/2005 | Shalev | |
| 2005/0187589 A1 | 8/2005 | Wallace et al. | |
| 2005/0203599 A1 | 9/2005 | Garabedian et al. | |
| 2005/0203600 A1 | 9/2005 | Wallace et al. | |
| 2005/0203602 A1 | 9/2005 | Wallace et al. | |
| 2005/0222647 A1 | 10/2005 | Wahlstrand et al. | |
| 2005/0277996 A1 | 12/2005 | Podhajsky et al. | |
| 2006/0030895 A1 | 2/2006 | Simon et al. | |
| 2006/0106430 A1 | 5/2006 | Fowler et al. | |
| 2006/0224223 A1 | 10/2006 | Podhajsky et al. | |
| 2006/0293723 A1 | 12/2006 | Whitehurst et al. | |
| 2007/0000784 A1 | 1/2007 | Paul et al. | |
| 2007/0073402 A1 | 3/2007 | Vresilovic et al. | |
| 2007/0162086 A1 | 7/2007 | DiLorenzo | |
| 2007/0213700 A1 | 9/2007 | Davison et al. | |
| 2007/0233202 A1 | 10/2007 | Wallace et al. | |
| 2007/0255338 A1* | 11/2007 | Wahlstrand | A61N 1/36082 607/45 |
| 2008/0009927 A1 | 1/2008 | Vilims | |
| 2008/0119907 A1 | 5/2008 | Stahmann | |
| 2008/0260542 A1 | 10/2008 | Nishikawa et al. | |
| 2009/0112278 A1 | 4/2009 | Wingeier et al. | |
| 2009/0125080 A1 | 5/2009 | Montgomery | |
| 2009/0126813 A1 | 5/2009 | Yanagisawa et al. | |
| 2009/0131850 A1* | 5/2009 | Geiger | A61M 27/006 604/9 |
| 2009/0312816 A1* | 12/2009 | Gross | A61N 1/205 607/51 |
| 2010/0217369 A1 | 8/2010 | Gross | |
| 2010/0324441 A1 | 12/2010 | Hargrove et al. | |
| 2011/0046540 A1 | 2/2011 | Alterman et al. | |
| 2011/0054518 A1 | 3/2011 | Carbunaru et al. | |
| 2011/0160638 A1* | 6/2011 | Mauge | A61M 27/006 604/9 |
| 2011/0160797 A1 | 6/2011 | Makous et al. | |
| 2012/0053659 A1 | 3/2012 | Molnar et al. | |
| 2012/0203307 A1 | 8/2012 | Schroeppel et al. | |
| 2013/0066392 A1 | 3/2013 | Simon et al. | |
| 2013/0102952 A1 | 4/2013 | Gross | |
| 2013/0166006 A1 | 6/2013 | Williams | |
| 2013/0289385 A1 | 10/2013 | Lozano et al. | |
| 2014/0058189 A1 | 2/2014 | Stubbeman | |
| 2014/0088672 A1 | 3/2014 | Bedenbaugh | |
| 2014/0207224 A1 | 7/2014 | Simon | |
| 2014/0257168 A1 | 9/2014 | Gill | |
| 2014/0324128 A1 | 10/2014 | Gross | |
| 2015/0011927 A1 | 1/2015 | Hua | |
| 2015/0119898 A1 | 4/2015 | Desalles et al. | |
| 2016/0331970 A1 | 11/2016 | Lozano | |
| 2017/0007823 A1 | 1/2017 | Gross | |
| 2017/0120053 A1 | 5/2017 | Fostick et al. | |

FOREIGN PATENT DOCUMENTS

| | | |
|---|---|---|
| WO | 94/05369 | 3/1994 |
| WO | 01/52931 | 7/2001 |
| WO | 01/85027 | 11/2001 |
| WO | 2001/085094 | 11/2001 |
| WO | 2006/090397 | 8/2006 |
| WO | 2008/007369 | 1/2008 |
| WO | 2017/072769 | 5/2017 |

OTHER PUBLICATIONS

Sawyer, P N et al. "Measurement of streaming potentials of mammalian blood vessels, aorta and vena cava, in vivo." Biophysical journal vol. 6,5 (1966): 641-51. doi:10.1016/S0006-3495(66)86683-3, https://www.ncbi.nlm.nih.gov/pmc/articles/PMC1368020/, viewed on Jul. 22, 2019.*

An Office Action dated Apr. 25, 2018, which issued during the prosecution of U.S. Appl. No. 15/637,330.

An Office Action dated Mar. 25, 2019, which issued during the prosecution of U.S. Appl. No. 15/742,245.

International Search Report and Written Opinion dated May 23, 2019 from the International Searching Authority in application No. PCT/IL2019/050284.

Non-Final Office Action dated Nov. 29, 2019 issued in U.S. Appl. No. 15/969,411.

Communication dated Aug. 24, 2020 from Japanese Patent Office in JP Application No. 2018-521586.

Karran, E. et al, "The Amyloid cascade hypothesis for Alzheimer's Disease: an appraisal for the development of therapeutics," Nature Reviews Drug Discovery, Sep. 2011, vol. 10; 698-712.

De La Torre, J.C., "Vascular Basis of Alzheimer's Pathogenesis," Ann NY Acad. Sci. 977:196-215 (Nov. 2002).

Weller, Roy O. et al, "Perivascular Drainage of Amyloid-β Peptides from the Brain and Its Failure in Cerebral Amyloid Angiopathy and Alzheimer's Disease," Brain Pathology 18 (Apr. 2008) 253-266.

Brief PubMed search for metal ions in Alzheimer.

An Office Action dated Sep. 27, 2016, which issued during the prosecution of U.S. Appl. No. 14/926,705.

An International Search Report and a Written Opinion both dated Aug. 7, 2008, which issued during the prosecution of Applicant's PCT/IL2007/000865.

An Office Action dated Mar. 29, 2013, which issued during the prosecution of U.S. Appl. No. 12/373,306.

An Office Action dated Oct. 31, 2011, which issued during the prosecution of U.S. Appl. No. 12/373,306.

(56) References Cited

OTHER PUBLICATIONS

An Office Action dated Oct. 1, 2012, which issued during the prosecution of U.S. Appl. No. 12/373,306.
Notice of Allowance dated Jul. 24, 2013, which issued during the prosecution of U.S. Appl. No. 12/373,306.
An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann, I.M. et al., "In-vitro evaluation of a drainage catheter with integrated bioimpedance electrodes to determine ventricular size," Biomed Tech 2013; 58 (Suppl. 1) Sep. 2013 (2 pages total).
An Office Action dated Aug. 31, 2015, which issued during the prosecution of U.S. Appl. No. 13/872,794.
An Applicant Initiated Interview Summary dated Dec. 14, 2015, which issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26, 2017, which issued during the prosecution of Applicant's PCT/IL2016/051161.
Notice of Allowance dated Jul. 14, 2017, which issued during the prosecution of U.S. Appl. No. 13/872,794.
An Office Action dated May 26, 2017, which issued during the prosecution of U.S. Appl. No. 15/453,290.
An International Preliminary Report on Patentability dated Apr. 7, 2009, which issued during the prosecution of Applicant's PCT/IL2007/000865.
Loutzenhiser, L. et al., "Membrane Potential measurements in renal afferent and efferent arterioles: actions of Angiotensin II", American Journal of Physiology—Renal Physiol. Aug. 1, 1997 vol. 273 No. 2 F307-F314.
U.S. Appl. No. 60/830,717, filed Jul. 12, 2006.
Dao-Sheng, Liu et al., "Activation of Na+ and K+ Pumping Modes of (Na,K)-ATPase by an Oscillating Electric Field," The Journal of Biological Chemistry, vol. 265. No. 13, May 5, 1990. (pp. 7260-7267).
Service, Robert F. "Electric fields deliver drugs into tumors." http://news.sciencemaa.ora. Feb. 4, 2015. (5 Pages Total).
Vernengo J., "Injectable Bioadhesive Hydrogels for Nucleus Pulposus Replacement and Repair of the Damaged Intervertebral Disc: A Thesis," Drexel University (Jan. 2007).
Urban, J. P. G. et al., "The nucleus of the intervertebral disc from development to degeneration," American Zoologist 40(1): 53-61 (2000).
Cheung, K. M. C. et al., "Intervertebral disc regeneration by use of autologous mesenchymal stem cells, an experimental model in rabbits," Abstract from the SRS 2004 Annual Meeting.
Freemont, T.J. et al., "Degeneration of intervertebral discs: current understanding of cellular and molecular events, and implications for novel therapies," Expert Reviews in Molecular Biology, Mar. 29, 2001 (Cambridge University Press).
An Office Action dated Sep. 12, 2011, which issued during the prosecution of U.S. Appl. No. 12/373,306.
An Office Action dated Jul. 24, 2017, which issued during the prosecution of U.S. Appl. No. 14/982,187.
An International Search Report and a Written Opinion both dated Mar. 10, 2017, which issued during the prosecution of Applicant's PCT/IL2016/051363.
Office Action dated Jan. 22, 2020 issued in U.S. Appl. No. 15/771,551.
Communication dated Nov. 20, 2020 by the United States Patent and Trademark Office in U.S. Appl. No. 16/353,407.

\* cited by examiner

ELECTRICAL TREATMENT OF HYDROCEPHALUS

CROSS-REFERENCES TO RELATED APPLICATIONS

The present application is a continuation of U.S. patent application Ser. No. 13/872,794, filed Apr. 29, 2013, now U.S. Pat. No. 9,731,122.

U.S. patent application Ser. No. 13/872,794, filed Apr. 29, 2013, is related to U.S. patent application Ser. No. 13/663,757 to Gross, filed Oct. 30, 2012, now U.S. Pat. No. 8,676,348, which is a continuation of U.S. patent application Ser. No. 12/373,306 to Gross, now U.S. Pat. No. 8,577,469, which is a US National Phase of PCT patent application PCT/IL07/00865 to Gross, filed Jul. 10, 2007, entitled "Iontophoretic and electroosmotic disc treatment", which published as WO 2008/007369; which claims priority from U.S. provisional patent application 60/830,717 to Gross, filed Jul. 12, 2006, entitled "Iontophoretic and electroosmotic disc treatment", all of which are incorporated herein by reference.

FIELD OF THE INVENTION

The present invention relates generally to medical devices, and specifically to apparatus and methods for increasing the throughput of fluid through a tissue or otherwise modifying the fluid balance in a tissue.

BACKGROUND

Many ailments originate from excess fluid in tissues, e.g., due to insufficient or damaged drainage of fluid from the tissue. As a result, this fluid causes elevated pressure in the tissue, which may result in discomfort and/or tissue damage. Examples of tissues prone to this problem are the brain, kidneys, lymph nodes, and eyes.

For hydrocephalus (i.e., the abnormal accumulation of cerebrospinal fluid in the ventricles of the brain), a common treatment approach is to use a shunt, which includes a drainage tube and a valve that controls the volume and rate of cerebrospinal fluid outflow from the brain to another part of the body (e.g., the abdomen).

SUMMARY OF THE INVENTION

Techniques are described for electroosmotically driving fluid between a first tissue of a subject and a second tissue of the subject. For some applications, the fluid is driven in response to detecting a pressure at at least one of the tissues, and/or a pressure difference between the tissues. For some applications, the pressure difference is detected by detecting a voltage, such as a streaming potential, between the tissues.

For some applications of the present invention, a system for increasing the throughput of fluid in the brain is provided. Typically, a first electrode is coupled to the superior sagittal sinus of the subject, and a second electrode is coupled to the cerebral cortex of the subject. According to one application of the present invention, a control unit, coupled to the electrodes, is configured to apply a voltage between the first and second electrodes, and to configure the voltage to electroosmotically drive fluid from the superior sagittal sinus to the cerebral cortex.

For some applications of the present invention, a system for increasing the throughput of fluid in the kidney is provided. Typically, a first electrode is coupled to the renal artery of the subject, and a second electrode is coupled to the ureter of the subject. According to one application of the present invention, the control unit is configured to apply a voltage between the first and second electrodes, and to configure the voltage to electroosmotically drive fluid from the renal artery to the ureter.

For some applications of the present invention, a system for increasing the throughput of fluid in a lymph node is provided. Typically, a first electrode is coupled to the artery entering the lymph node of the subject, and a second electrode is coupled to the medullary sinus of the lymph node. According to one application of the present invention, the control unit is configured to apply a voltage between the first and second electrodes, and to configure the voltage to electroosmotically drive fluid from the artery entering the lymph node to the medullary sinus.

For some applications of the present invention, a system for increasing the throughput of fluid in the eye is provided. Typically, a first electrode is coupled to a vitreous cavity of the eye of the subject, and a second electrode is coupled to a Schlemm's canal of the subject. According to one application of the present invention, the control unit is configured to apply a voltage between the first and second electrodes, and to configure the voltage to electroosmotically drive fluid from the vitreous cavity to the Schlemm's canal.

For some applications of the present invention, a system for driving fluid between a nucleus pulposus of an intervertebral disc and a site outside of the nucleus pulposus is provided. Typically, a first electrode is coupled to (e.g., inserted into) the nucleus pulposus of the subject, and a second electrode is coupled to the site outside of the nucleus pulposus (e.g., to an outer surface of an annulus fibrosus of the intervertebral disc). According to one application of the present invention, the control unit is configured to apply a voltage between the first and second electrodes, and to configure the voltage to electroosmotically drive fluid from the site outside of the nucleus pulposus, to the nucleus pulposus.

For some applications of the present invention, electroosmosis is performed using insulated electrodes. Typically, when the control unit applies a voltage between the electrodes, a capacitance-based current flows toward one of the electrodes, resulting in fluid electroosmotically moving from one site to another. For example, this technique may be practiced to drive fluid in any of the sites described hereinabove.

It is noted that, for some applications, electroosmosis techniques as provided herein can be performed anywhere in a body of the subject where ionic filtration occurs.

There is further provided, in accordance with an application of the present invention, apparatus for driving fluid between first and second anatomical sites of a subject, the apparatus including:

a first electrode, configured to be coupled to the first anatomical site of the subject;

a second electrode, configured to be coupled to the second anatomical site of the subject; and a control unit, configured to:

detect a pressure difference between the first and second anatomical sites, and in response to the detected pressure difference, drive fluid between the first and second anatomical sites by applying a treatment voltage between the first and second electrodes.

In an application, the control unit is configured to provide a rest period during which the treatment voltage is not applied, and to apply, between the first and second electrodes, an opposite voltage that is opposite to the treatment voltage and that has a lower magnitude than the treatment voltage.

In an application, each electrode is insulated such that no portion of the electrode may be in electrical contact with any tissue of the subject, and the control unit is configured to drive a capacitative current between the first and second insulated electrodes by applying the treatment voltage between the electrodes.

In an application, the apparatus further includes a pressure sensor, and the apparatus is configured to detect the pressure difference by the pressure sensor being configured to detect the pressure difference.

In an application, the pressure sensor includes a mechanical pressure sensor, configured to detect the pressure difference at least in part by detecting mechanical pressure pressing on a component of the pressure sensor.

In an application, the pressure sensor includes at least a first mechanical pressure sensor, configured to detect the pressure at the first anatomical site, and a second mechanical pressure sensor, configured to detect the pressure at the second anatomical site.

In an application, the apparatus is configured to detect the pressure difference by detecting a voltage between the first and second electrodes, and the control unit is configured to apply the treatment in response to the detected pressure difference by being configured to apply the treatment voltage in response to the detected voltage.

In an application, the apparatus is configured to detect the detected voltage by being configured to detect a streaming voltage.

In an application, the apparatus is configured not to apply the treatment voltage while detecting the detected voltage.

In an application, the control unit includes voltage-detecting circuitry, configured to detect the voltage.

In an application, the first anatomical site includes a superior sagittal sinus of the subject, the second anatomical site includes a cerebral cortex of the subject, and the control unit is configured to electroosmotically drive the fluid by electroosmotically driving the fluid between the superior sagittal sinus and the cerebral cortex of the subject.

In an application, the control unit is configured to electroosmotically drive the fluid from the cerebral cortex to the superior sagittal sinus of the subject.

In an application, the control unit is configured to detect the pressure by being configured to detect a voltage between the first and second electrodes.

In an application, the first anatomical site includes a renal artery of the subject, the second anatomical site includes a ureter of the subject, and the control unit is configured to configure the treatment voltage to electroosmotically drive the fluid by electroosmotically driving the fluid between the renal artery and the ureter of the subject.

In an application, the control unit is configured to electroosmotically drive the fluid from the renal artery to the ureter of the subject.

In an application, the control unit is configured to detect the pressure by being configured to detect a voltage between the first and second electrodes.

In an application, the first anatomical site includes an artery entering a lymph node of the subject, the second anatomical site includes a medullary sinus of the lymph node of the subject, and the control unit is configured to electroosmotically drive the fluid by electroosmotically driving the fluid between the artery and the medullary sinus of the subject.

In an application, the control unit is configured to electroosmotically drive the fluid from the artery to the medullary sinus of the subject.

In an application, the control unit is configured to detect the pressure by being configured to detect a voltage between the first and second electrodes, and to apply the treatment voltage only when the detected voltage is greater than.

In an application, the first anatomical site includes a vitreous cavity of an eye of the subject, the second anatomical site includes a Schlemm's canal of the subject, and the control unit is configured to electroosmotically drive the fluid by electroosmotically driving the fluid between the vitreous cavity and the Schlemm's canal of the subject.

In an application, the control unit is configured to electroosmotically drive the fluid from the vitreous cavity to the Schlemm's canal of the subject.

In an application, the control unit is configured to detect the pressure by being configured to detect a voltage between the first and second electrodes.

In an application, the first anatomical site includes a site within a subarachnoid cavity of the subject, the second anatomical site includes a site outside of the subarachnoid cavity of the subject, and the control unit is configured to electroosmotically drive the fluid by electroosmotically driving the fluid between the site within the subarachnoid cavity and the site outside of the subarachnoid cavity of the subject.

In an application, the control unit is configured to electroosmotically drive the fluid from the site within the subarachnoid cavity to the site outside of the subarachnoid cavity of the subject.

In an application, the control unit is configured to detect the pressure by being configured to detect a voltage between the first and second electrodes.

There is further provided, in accordance with an application of the present invention, a method, including: detecting a pressure difference between a first anatomical site and a second anatomical site of a subject; and in response to the detected pressure difference, electroosmotically driving fluid between the first and second anatomical sites by applying a treatment voltage between the first and second anatomical sites.

In an application, the method further includes providing a rest period during which the treatment voltage is not applied, and applying, during the rest period, an opposite voltage between the first and second anatomical sites, the opposite voltage being opposite to the treatment voltage and having a lower magnitude than the treatment voltage.

In an application, the method further includes implanting a first electrode at the first anatomical site, and implanting a second electrode at the second anatomical site, and applying the treatment voltage between the first and second anatomical sites includes applying the treatment voltage between the first and second electrodes.

In an application:

implanting the first electrode includes implanting a first insulated electrode, such that no portion of the first insulated electrode is in electrical contact with any tissue of the subject, implanting the second electrode includes implanting a second insulated electrode, such that no portion of the second insulated electrode is in electrical contact with any tissue of the subject, and applying the treatment voltage includes driving a capacitative current between the first and second insulated electrodes.

In an application, detecting the pressure difference includes detecting the pressure difference using at least one mechanical pressure sensor.

In an application, detecting the pressure difference includes detecting a pressure at the first anatomical site using a first mechanical pressure sensor, and detecting a pressure at the second anatomical site using a second mechanical pressure sensor.

In an application, detecting the pressure difference includes detecting the pressure difference by detecting a voltage between the first and second electrodes, and applying the treatment voltage in response to the detected pressure difference includes applying the treatment voltage in response to the detected voltage.

In an application, detecting the detected voltage includes detecting a streaming voltage.

In an application, applying the treatment voltage includes not applying the treatment voltage while detecting the detected voltage.

In an application:
the first anatomical site includes a superior sagittal sinus of the subject,
the second anatomical site includes a cerebral cortex of the subject, and
electroosmotically driving the fluid between the first and second anatomical sites includes electroosmotically driving the fluid between the superior sagittal sinus and the cerebral cortex of the subject.

In an application, driving the fluid between the superior sagittal sinus and the cerebral cortex of the subject includes driving the fluid from the cerebral cortex to the superior sagittal sinus of the subject.

In an application, detecting the pressure difference includes detecting the pressure difference by detecting a voltage between the first and second electrodes.

In an application:
the first anatomical site includes a renal artery of the subject,
the second anatomical site includes a ureter of the subject, and
electroosmotically driving the fluid between the first and second anatomical sites includes electroosmotically driving the fluid between the renal artery and the ureter of the subject.

In an application, driving the fluid between the renal artery and the ureter of the subject includes driving the fluid from the renal artery to the ureter of the subject.

In an application, detecting the pressure difference includes detecting the pressure difference by detecting a voltage between the first and second electrodes.

In an application:
the first anatomical site includes an artery entering a lymph node of the subject,
the second anatomical site includes a medullary sinus of the lymph node of the subject, and
electroosmotically driving the fluid between the first and second anatomical sites includes electroosmotically driving the fluid between the artery entering a lymph node and the medullary sinus of the subject.

In an application, driving the fluid between the artery entering the lymph node and the medullary sinus of the subject includes driving the fluid from the medullary sinus to the artery entering the lymph node of the subject.

In an application, detecting the pressure difference includes detecting the pressure difference by detecting a voltage between the first and second electrodes.

In an application:
the first anatomical site includes a vitreous cavity of an eye of the subject,
the second anatomical site includes a Schlemm's canal of the eye of the subject, and
electroosmotically driving the fluid between the first and second anatomical sites includes electroosmotically driving the fluid between the vitreous cavity and the Schlemm's canal of the subject.

In an application, driving the fluid between the vitreous cavity and the Schlemm's canal of the subject includes driving the fluid from the vitreous cavity to the Schlemm's canal of the subject.

In an application, detecting the pressure difference includes detecting the pressure difference by detecting a voltage between the first and second electrodes.

In an application:
the first anatomical site includes a nucleus pulposus of an intervertebral disc of the subject,
the second anatomical site includes a site outside of the nucleus pulposus of the disc of the subject, and
electroosmotically driving the fluid between the first and second anatomical sites includes electroosmotically driving the fluid between the nucleus pulposus and the site outside of the nucleus pulposus of the subject.

In an application, driving the fluid between the nucleus pulposus and the site outside of the nucleus pulposus of the subject includes driving the fluid from the nucleus pulposus to the site outside of the nucleus pulposus of the subject.

In an application, driving the fluid between the nucleus pulposus and the site outside of the nucleus pulposus of the subject includes driving the fluid from the site outside of the nucleus pulposus to the nucleus pulposus of the subject.

In an application, detecting the pressure difference includes detecting the pressure difference by detecting a voltage between the first and second electrodes.

In an application:
the first anatomical site includes a site within a subarachnoid cavity of the subject,
the second anatomical site includes a site outside of the subarachnoid cavity of the subject, and
electroosmotically driving the fluid between the first and second anatomical sites includes electroosmotically driving the fluid between the site within the subarachnoid cavity of the subject and the site outside of the subarachnoid cavity of the subject.

In an application, driving the fluid between the site within the subarachnoid cavity and the site outside of the subarachnoid cavity of the subject includes driving the fluid from the site within the subarachnoid cavity to the site outside of the subarachnoid cavity of the subject.

In an application, detecting the pressure difference includes detecting the pressure difference by detecting a voltage between the first and second electrodes.

There is further provided, in accordance with an application of the present invention, a method, including:
electroosmotically driving fluid between a superior sagittal sinus of a subject and a cerebral cortex of the subject, by applying a treatment voltage between the superior sagittal sinus and the cerebral cortex of the subject.

In an application, the method further includes providing a rest period during which the treatment voltage is not applied, and applying, during the rest period, an opposite voltage between the superior sagittal sinus and the cerebral cortex, the opposite voltage being opposite to the treatment voltage and having a lower magnitude than the treatment voltage.

In an application, applying the treatment voltage includes applying a capacitative current.

In an application, driving the fluid between the superior sagittal sinus and the cerebral cortex of the subject includes driving the fluid from the cerebral cortex to the superior sagittal sinus of the subject.

In an application, the method further includes detecting a pressure difference between the superior sagittal sinus of the subject and the cerebral cortex of the subject, and applying the treatment voltage includes applying the treatment voltage in response to the detected pressure difference.

In an application, detecting the pressure difference includes detecting a voltage between the superior sagittal sinus of the subject and the cerebral cortex of the subject, and applying the treatment voltage includes applying the treatment voltage in response to the detected voltage.

In an application, detecting the detected voltage includes detecting a streaming potential.

In an application, the method further includes implanting a first electrode at the superior sagittal sinus of the subject, and a second electrode at the cerebral cortex of the subject, and detecting the voltage between the superior sagittal sinus of the subject and the cerebral cortex of the subject includes detecting a voltage between the first and second electrodes.

There is further provided, in accordance with an application of the present invention, a method, including:

electroosmotically driving fluid between a renal artery of a subject and a ureter of the subject, by applying a treatment voltage between the renal artery and the ureter of the subject.

In an application, the method further includes providing a rest period during which the treatment voltage is not applied, and applying, during the rest period, an opposite voltage between the renal artery and the ureter, the opposite voltage being opposite to the treatment voltage and having a lower magnitude than the treatment voltage.

In an application, applying the treatment voltage includes applying a capacitative current.

In an application, driving the fluid between the renal artery and the ureter of the subject includes driving the fluid from the renal artery to the ureter of the subject.

In an application, the method further includes detecting a pressure difference between the renal artery of the subject and the ureter of the subject, and applying the treatment voltage includes applying the treatment voltage in response to the detected pressure difference.

In an application, detecting the pressure difference includes detecting a voltage between the renal artery of the subject and the ureter of the subject, and applying the treatment voltage includes applying the treatment voltage in response to the detected voltage.

In an application, detecting the detected voltage includes detecting a streaming potential.

In an application, the method further includes implanting a first electrode at the renal artery of the subject, and a second electrode at the ureter of the subject, and detecting the voltage between the renal artery of the subject and the ureter of the subject includes detecting a voltage between the first and second electrodes.

There is further provided, in accordance with an application of the present invention, a method, including:

electroosmotically driving fluid between an artery entering a lymph node of a subject and a medullary sinus of the lymph node of the subject, by applying a treatment voltage between the artery and the medullary sinus of the subject.

In an application, the method further includes providing a rest period during which the treatment voltage is not applied, and applying, during the rest period, an opposite voltage between the artery and the medullary sinus, the opposite voltage being opposite to the treatment voltage and having a lower magnitude than the treatment voltage.

In an application, applying the treatment voltage includes applying a capacitative current.

In an application, driving the fluid between the artery entering the lymph node and the medullary sinus of the subject includes driving the fluid from the medullary sinus to the artery entering the lymph node of the subject.

In an application, the method further includes detecting a pressure difference between the artery of the subject and the medullary sinus of the subject, and applying the treatment voltage includes applying the treatment voltage in response to the detected pressure difference.

In an application, detecting the pressure difference includes detecting a voltage between the artery of the subject and the medullary sinus of the subject, and applying the treatment voltage includes applying the treatment voltage in response to the detected voltage.

In an application, detecting the detected voltage includes detecting a streaming potential.

In an application, the method further includes implanting a first electrode at the artery of the subject, and a second electrode at the medullary sinus of the subject, and detecting the voltage between the artery of the subject and the medullary sinus of the subject includes detecting a voltage between the first and second electrodes.

There is further provided, in accordance with an application of the present invention, a method, including:

electroosmotically driving fluid between a vitreous cavity of an eye of a subject and a Schlemm's canal of the eye of the subject, by applying a treatment voltage between the vitreous cavity and the Schlemm's canal of the subject.

In an application, the method further includes providing a rest period during which the treatment voltage is not applied, and applying, during the rest period, an opposite voltage between the vitreous cavity and the Schlemm's canal, the opposite voltage being opposite to the treatment voltage and having a lower magnitude than the treatment voltage.

In an application, applying the treatment voltage includes applying a capacitative current.

In an application, driving the fluid between the vitreous cavity and the Schlemm's canal of the subject includes driving the fluid from the vitreous cavity to the Schlemm's canal of the subject.

In an application, the method further includes detecting a pressure difference between the vitreous cavity of the subject and the Schlemm's canal of the subject, and applying the treatment voltage includes applying the treatment voltage in response to the detected pressure difference.

In an application, detecting the pressure difference includes detecting a voltage between the vitreous cavity of the subject and the Schlemm's canal of the subject, and applying the treatment voltage includes applying the treatment voltage in response to the detected voltage.

In an application, detecting the detected voltage includes detecting a streaming potential.

In an application, the method further includes implanting a first electrode at the vitreous cavity of the subject, and a second electrode at the Schlemm's canal of the subject, and detecting the voltage between the vitreous cavity of the subject and the Schlemm's canal of the subject includes detecting a voltage between the first and second electrodes.

There is further provided, in accordance with an application of the present invention, a method, including:

electroosmotically driving fluid between a site within a subarachnoid cavity of a subject and a site outside of the subarachnoid cavity of the subject, by applying a treatment voltage between the site within the subarachnoid cavity and the site outside of the subarachnoid cavity of the subject.

In an application, the method further includes providing a rest period during which the treatment voltage is not applied, and applying, during the rest period, an opposite voltage between the site within the subarachnoid cavity and the site outside of the subarachnoid cavity, the opposite voltage being opposite to the treatment voltage and having a lower magnitude than the treatment voltage.

In an application, electroosmotically driving the fluid by applying the treatment voltage includes electroosmotically driving fluid between a site within a subarachnoid cavity of a subject that is asymptomatic of Alzheimer's disease and a site outside of the subarachnoid cavity of the subject, by applying a treatment voltage between the site within the subarachnoid cavity and the site outside of the subarachnoid cavity of the subject that is asymptomatic of Alzheimer's disease.

In an application, applying the treatment voltage includes applying a capacitative current.

In an application, driving the fluid between the site within the subarachnoid cavity and the site outside of the subarachnoid cavity of the subject includes driving the fluid from the site within the subarachnoid cavity to the site outside of the subarachnoid cavity of the subject.

In an application, the method further includes detecting a pressure difference between the site within the subarachnoid cavity of the subject and the site outsider of the subarachnoid cavity of the subject, and applying the treatment voltage includes applying the treatment voltage in response to the detected pressure difference.

In an application, detecting the pressure difference includes detecting a voltage between the site within the subarachnoid cavity of the subject and the site outside of the subarachnoid cavity of the subject, and applying the treatment voltage includes applying the treatment voltage in response to the detected voltage.

In an application, detecting the detected voltage includes detecting a streaming potential.

In an application, the method further includes implanting a first electrode at the site within the subarachnoid cavity of the subject, and a second electrode at the site outside of the subarachnoid cavity of the subject, and detecting the voltage between the site within the subarachnoid cavity of the subject and the site outside of the subarachnoid cavity of the subject includes detecting a voltage between the first and second electrodes.

The present invention will be more fully understood from the following detailed description of applications thereof, taken together with the drawings, in which:

DETAILED DESCRIPTION OF EMBODIMENTS

Figure 1:
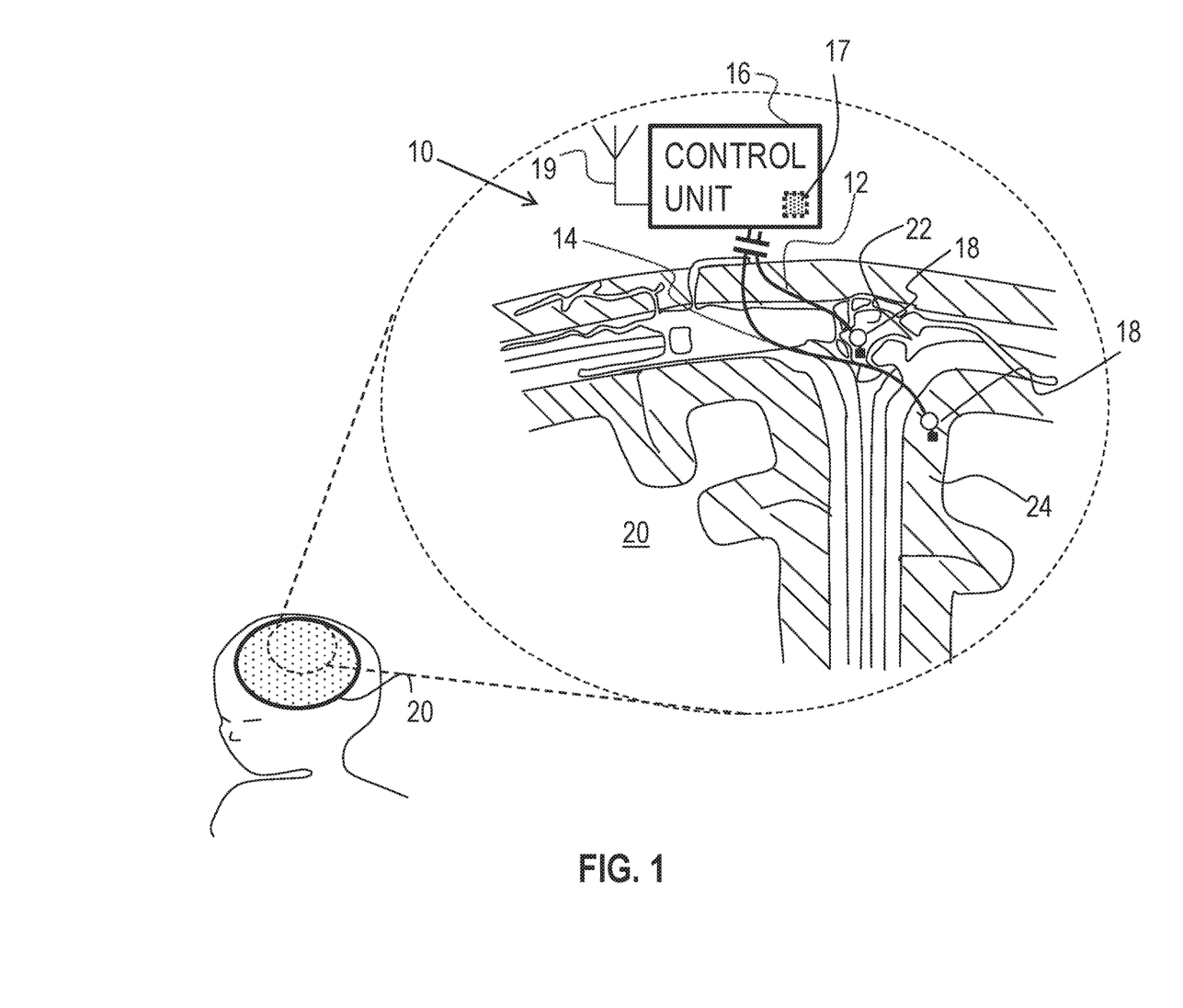
FIG. 1 is a schematic illustration of a system for altering throughput of fluid in the brain of a subject, in accordance with some applications of the present invention.

Reference is made to FIG. 1, which is a schematic illustration of medical apparatus 10, comprising a first electrode 12, a second electrode 14 and a control unit 16, for altering throughput of fluid in the brain of a subject, in accordance with some applications of the invention. According to one application of the present invention, medical apparatus 10 is coupled to a brain 20 of the subject. Typically, first electrode 12 is implanted at a superior sagittal sinus 22 of the subject. Typically, second electrode 14 is implanted at a cerebral cortex 24 of the subject. According to one application of the present invention, control unit 16 is configured to apply a treatment voltage between first electrode 12 and second electrode 14, and to configure the treatment voltage to electroosmotically drive fluid from cerebral cortex 24 to superior sagittal sinus 22. It is hypothesized that this driving of the fluid reduces intracranial pressure (e.g., pressure in the brain), and thereby may be used to treat a subject suffering from elevated intracranial pressure, such as a subject suffering from hydrocephalus or brain trauma. It is also hypothesized that, for some applications, this driving of the fluid may be used to treat a subject suffering from normal pressure hydrocephalus.

Typically, control unit 16 applies the treatment voltage as a direct current (DC). For some applications of the invention, the control unit is configured to apply the treatment voltage according to a pre-selected schedule, such as a duty cycle, such as for a few hours per day, such as when the subject is sleeping. For example, the control unit may be configured to be controlled and/or powered by an extracorporeal controller, such as a controller comprising a wireless transmitter, disposed in and/or in the vicinity of the subject's bed. For some applications, one or more rest periods during which the treatment voltage is not applied, are provided in the pre-selected schedule. It is hypothesized that for some applications, the rest period facilitates equilibration of charge in the body of the subject. For some such applications, during rest periods in which the treatment voltage is not being applied, an opposite voltage (i.e., a voltage having an opposite sign to the treatment voltage) having a different (e.g., lower) magnitude is applied.

For some applications of the invention, apparatus 10 is configured to detect a pressure at at least one of the electrodes (e.g., the pressure above atmospheric pressure, at the implantation site of the electrode), and to apply the treatment voltage in response to the detected pressure. For example, apparatus 10 may be configured to detect pressure at cerebral cortex 24, and to apply the treatment voltage if the detected pressure is greater than a threshold pressure.

For some applications of the present invention, apparatus 10 comprises a pressure sensor 18, configured to detect the pressure. For some applications of the invention, pressure sensor 18 comprises a mechanical transducer-based pressure sensor, as is known in the art. That is, for some applications, the pressure sensor is configured to detect the pressure by detecting the mechanical pressure pressing on a component of the pressure sensor. For some such applications, and as shown in FIG. 1, pressure sensor 18 is coupled to and/or integrated with at least one of the electrodes, such as electrode 12.

For some applications, apparatus 10 is configured to sense a pressure difference between the implantation sites of first electrode 12 and second electrode 14, and to apply the treatment voltage in response to the detected pressure difference. For example, and as shown in FIG. 1, apparatus 10 may comprise two or more pressure sensors 18, each pressure sensor being coupled to and/or integrated with a respective electrode, and control unit 16 being configured to sense the difference between the pressure detected by each pressure sensor.

Alternatively or additionally, apparatus 10 may sense the pressure difference by detecting a voltage, such as a streaming potential, between the electrodes, that is indicative of the pressure difference between the sites. For example, control unit 16 may comprise voltage-detecting circuitry 17, configured to detect the voltage between electrodes 12 and 14, and may be configured to apply the treatment voltage only if the detected voltage is greater than a threshold voltage. Typically, control unit 16 is configured to apply the voltage only when the detected voltage between first electrode 12 and second electrode 14 is greater than 2 mV (e.g., greater than 20 mV, but typically less than 500 mV, for example, less than 50 mV). For some such applications, apparatus 10 may be considered to comprise a pressure detector that comprises electrodes 12 and 14, and circuitry 17.

Typically, the detected voltage is detected while the treatment voltage is not applied. For example, control unit 16 may be configured to apply the treatment voltage and detect the detected voltage in a sequence, and/or to periodically stop applying the treatment voltage so as to detect the detected voltage.

For some applications of the invention, control unit 16 comprises a receiver 19 (e.g., an antenna), which receives power wirelessly from an extracorporeal device, e.g., a mattress-based transmitter, or a transmitter coupled to a belt, hat, eyeglasses, or clothing item of the subject. For some applications, receiver 19 of control unit 16 receives power wirelessly from an implanted transmitter coupled to a power source (e.g., a battery). Alternatively or additionally, the control unit receives power from a power source (e.g., a battery), which may be in a common housing with the control unit.

Figure 2:
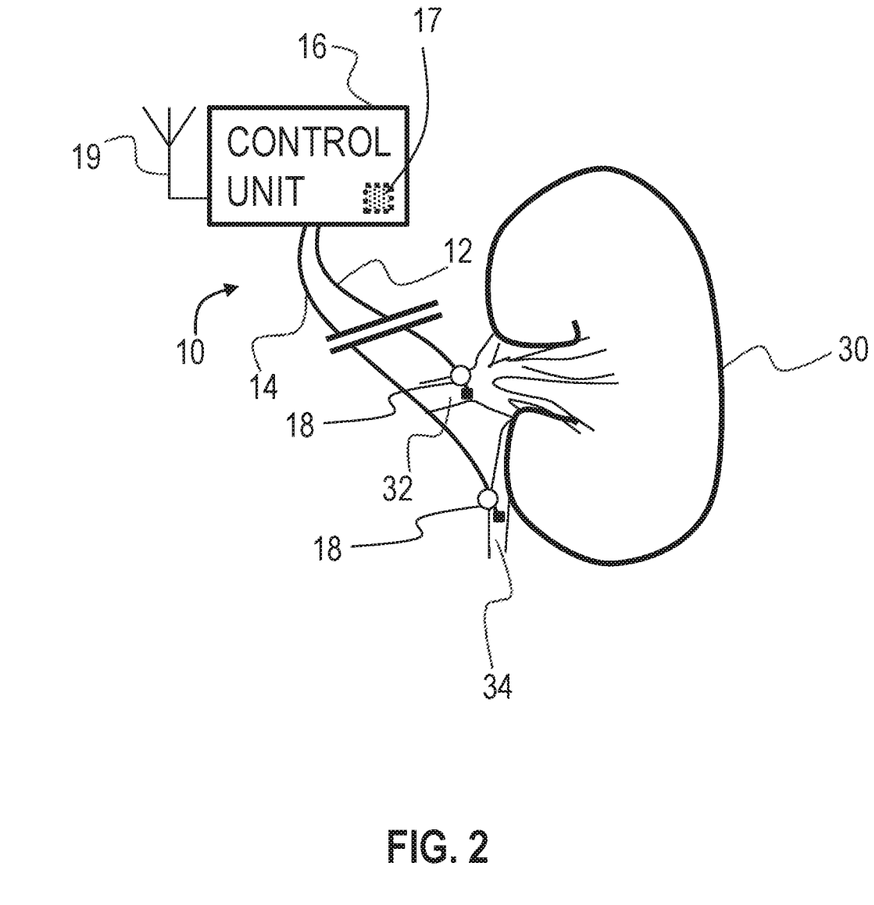
FIG. 2 is a schematic illustration of a system for altering throughput of fluid in a kidney of a subject, in accordance with some applications of the present invention.

Reference is now made to FIG. 2, which is a schematic illustration of medical apparatus 10, comprising generally the same components as shown in FIG. 1, being used to alter throughput of fluid in a kidney of a subject, in accordance with some applications of the invention. According to one application of the present invention, medical apparatus 10 is coupled to a kidney 30 of the subject. Typically, first electrode 12 is coupled to a renal artery 32 of the subject, and second electrode 14 is coupled to a ureter 34 of the subject. According to one application of the present invention, control unit 16 is configured to apply a voltage between first electrode 12 and second electrode 14, and to configure the voltage to electroosmotically drive fluid from renal artery 32 to ureter 34. It is hypothesized that this driving of the fluid is beneficial for subjects suffering from kidney disease and/or congestive heart failure (CHF).

As described with reference to FIG. 1, for some applications, apparatus 10 is configured to detect a pressure at at least one of the electrodes (e.g., the pressure above atmospheric pressure, at the implantation site of the electrode), and to apply the treatment voltage in response to the detected pressure. As also described with reference to FIG. 1, for some applications, apparatus 10 is configured to detect a pressure difference between the implantation sites of the electrodes, and to apply the treatment voltage in response to the detected pressure difference. As further described with reference to FIG. 1, for some such applications, apparatus 10 is configured to detect the pressure difference by detecting a voltage, such as a streaming potential, between the electrodes, that is indicative of the pressure difference between the sites. When apparatus 10 is implanted as shown in FIG. 2, the apparatus may thereby be configured to detect the pressure at renal artery 32 (e.g., the pressure above atmospheric pressure), and/or to detect the pressure difference and/or the voltage between the renal artery and ureter 34, and to apply the treatment voltage if the detected pressure, pressure difference, and/or voltage is greater than a threshold pressure, pressure difference, and/or voltage.

Typically, the detected voltage is detected while the treatment voltage is not applied. For example, control unit 16 may be configured to apply the treatment voltage and detect the detected voltage in a sequence, and/or to periodically stop applying the treatment voltage so as to detect the detected voltage.

Figure 3:
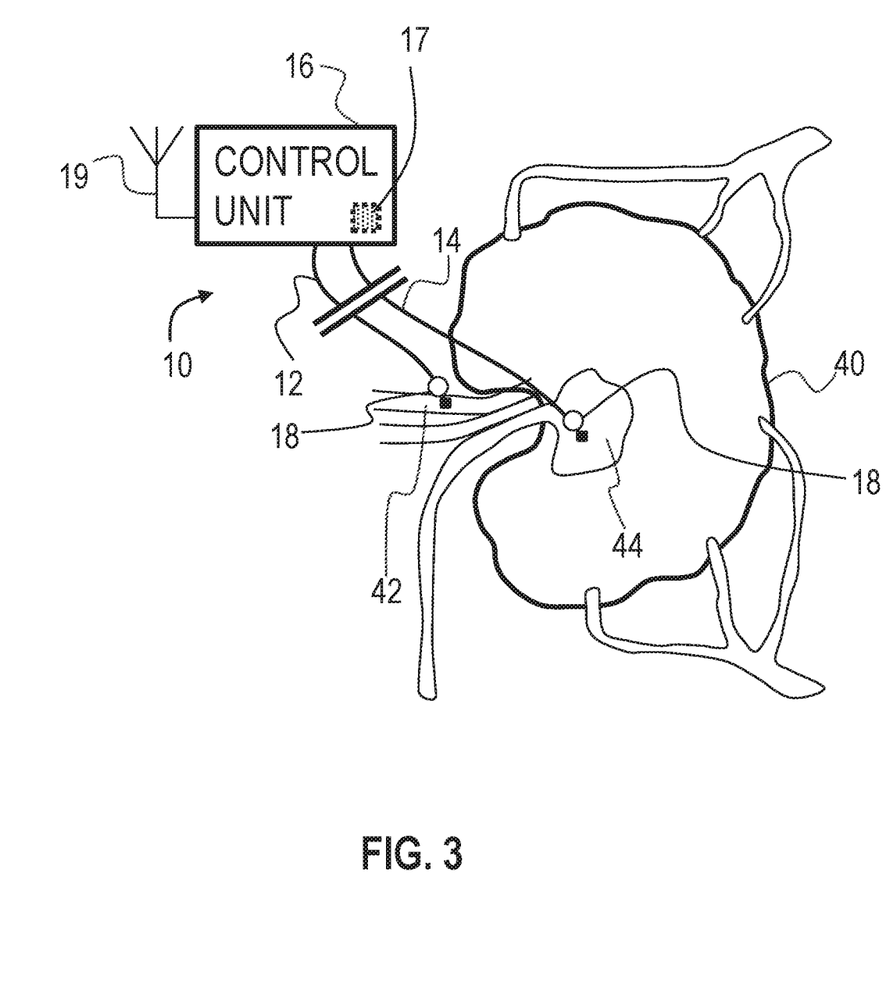
FIG. 3 is a schematic illustration of a system for altering throughput of fluid in a lymph node of a subject, in accordance with some applications of the present invention.

Reference is now made to FIG. 3, which is a schematic illustration of medical apparatus 10 for altering throughput of fluid in a lymph node of a subject, comprising generally the same components as shown in FIG. 1, in accordance with some applications of the invention. According to one application of the present invention, medical apparatus 10 is coupled to a lymph node 40 of the subject. Typically, first electrode 12 is coupled to a blood vessel, such as an artery 42 (or similarly a vein), in proximity to (e.g., entering) lymph node 40 of the subject, and second electrode 14 is coupled to a medullary sinus 44 of the lymph node (or at another site within the lymph node). According to one application of the present invention, control unit 16 is configured to apply a voltage between first electrode 12 and second electrode 14, and to configure the voltage to electroosmotically drive fluid from medullary sinus 44 toward (e.g., into) artery 42.

As described with reference to FIG. 1, for some applications, apparatus 10 is configured to detect a pressure at at least one of the electrodes (e.g., the pressure above atmospheric pressure, at the implantation site of the electrode), and to apply the treatment voltage in response to the detected pressure. As also described with reference to FIG. 1, for some applications, apparatus 10 is configured to detect a pressure difference between the implantation sites of the electrodes, and to apply the treatment voltage in response to the detected pressure difference. As further described with reference to FIG. 1, for some such applications, apparatus 10 is configured to detect the pressure difference by detecting a voltage, such as a streaming potential, between the electrodes, that is indicative of the pressure difference between the sites. When apparatus 10 is implanted as shown in FIG. 3, the apparatus may thereby be configured to detect the pressure at medullary sinus 44 (e.g., the pressure above atmospheric pressure), and/or to detect the pressure difference and/or the voltage between the medullary sinus and artery 42, and to apply the treatment voltage if the detected pressure, pressure difference, and/or voltage is greater than a threshold pressure, pressure difference, and/or voltage.

Typically, the detected voltage is detected while the treatment voltage is not applied. For example, control unit may be configured to apply the treatment voltage and detect the detected voltage in a sequence, and/or to periodically stop applying the treatment voltage so as to detect the detected voltage.

Figure 4:
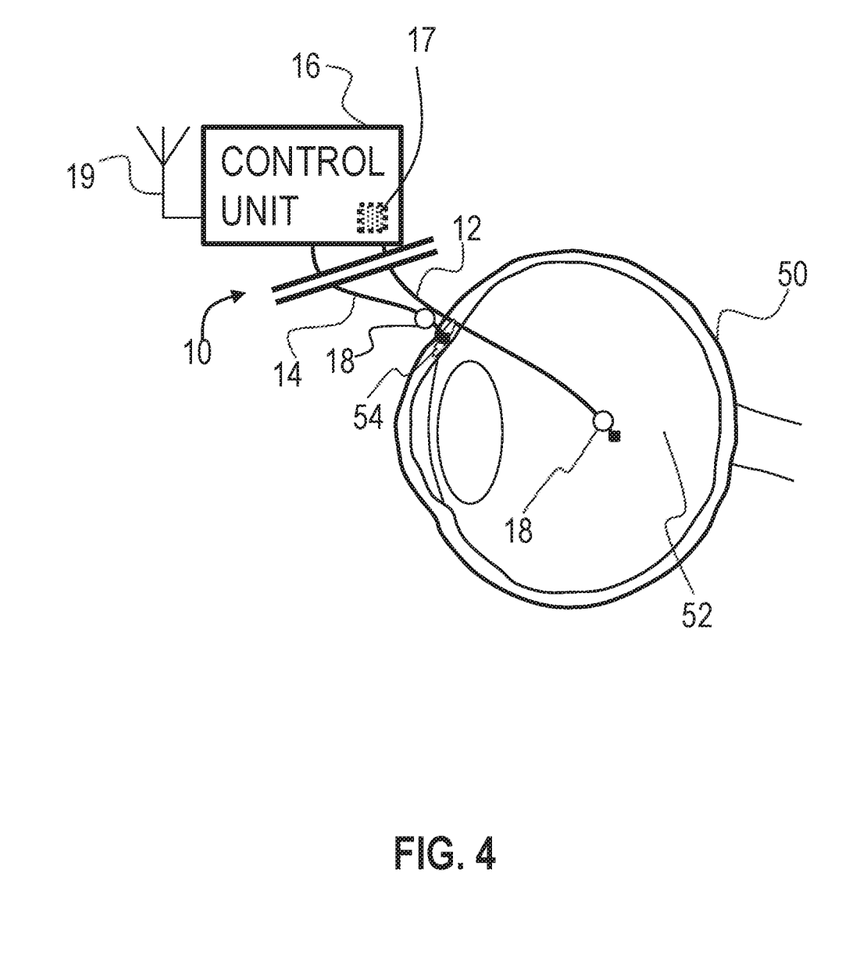
FIG. 4 is a schematic illustration of a system for altering throughput of fluid in an eye of a subject, in accordance with some applications of the present invention.

Reference is now made to FIG. 4, which is a schematic illustration of medical apparatus 10, comprising generally the same components as shown in FIG. 1, for altering throughput of fluid in an eye of a subject, in accordance with some applications of the invention. According to one application of the present invention, medical apparatus 10 is coupled to an eye 50 of the subject. Typically, first electrode 12 is coupled to a vitreous cavity 52, and second electrode 14 is coupled to Schlemm's canal 54 of the subject. According to one application of the present invention, control unit 16 is configured to apply a voltage between first electrode 12 and second electrode 14, and to configure the voltage to electroosmotically drive fluid from vitreous cavity 52 to Schlemm's canal 54 in order to reduce intraocular pressure.

As described with reference to FIG. 1, for some applications, apparatus 10 is configured to detect a pressure at at least one of the electrodes (e.g., the pressure above atmospheric pressure, at the implantation site of the electrode), and to apply the treatment voltage in response to the detected pressure. As also described with reference to FIG. 1, for some applications, apparatus 10 is configured to detect a pressure difference between the implantation sites of the electrodes, and to apply the treatment voltage in response to the detected pressure difference. As further described with reference to FIG. 1, for some such applications, apparatus 10 is configured to detect the pressure difference by detecting a voltage, such as a streaming potential, between the electrodes, that is indicative of the pressure difference between the sites. When apparatus 10 is implanted as shown in FIG. 4, the apparatus may thereby be configured to detect the pressure at vitreous cavity 52 (e.g., the pressure above atmospheric pressure), and/or to detect the pressure difference and/or the voltage between the vitreous cavity and Schlemm's canal 54, and to apply the treatment voltage if the detected pressure, pressure difference, and/or voltage is greater than a threshold pressure, pressure difference, and/or voltage.

Typically, the detected voltage is detected while the treatment voltage is not applied. For example, control unit 16 may be configured to apply the treatment voltage and detect the detected voltage in a sequence, and/or to periodically stop applying the treatment voltage so as to detect the detected voltage.

Figure 5:
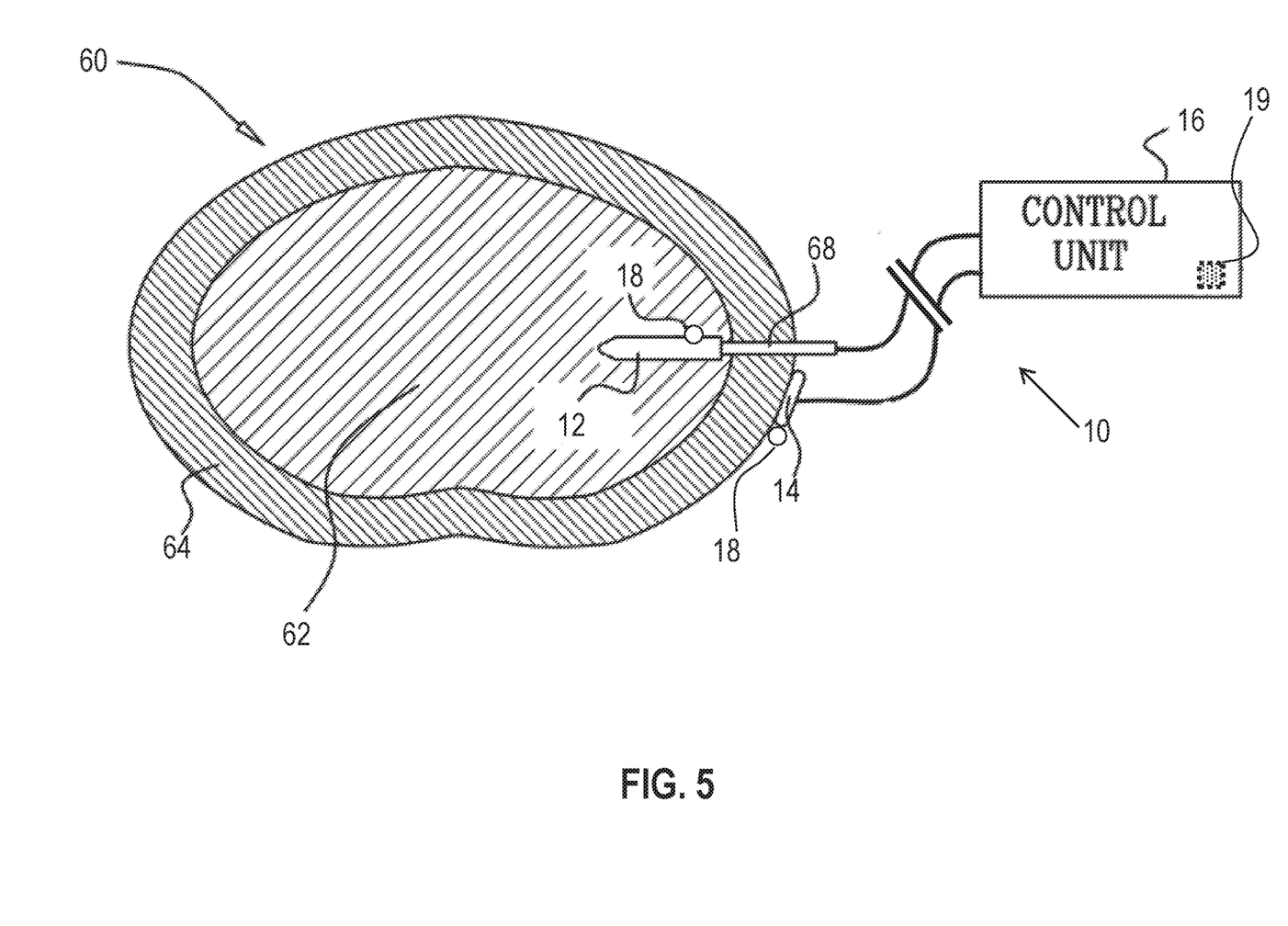
FIG. 5 is a schematic illustration of a system for sensing of the driving of fluid in an intervertebral disc of a subject, in accordance with some applications of the invention.

Reference is made to FIG. 5 which is a schematic illustration of medical apparatus 10, comprising generally the same components as shown in FIG. 1, for driving fluid in an intervertebral disc 60 of a subject, in accordance with some applications of the invention. According to one application of the present invention, medical apparatus 10 is coupled to disc 60 of the subject. Typically, first electrode 12 is implanted in a nucleus pulposus 62 of the disc, and second electrode 14 is implanted at a site outside of the nucleus pulposus, such as coupled to an outer surface of an annulus fibrosus 64 of the disc. For some applications, electrode 12 comprises a rigid support element having a non-conductive outer surface. The support element aids in the insertion of the electrode through annulus fibrosus 64 into nucleus pulposus 62, and in holding the electrode in place upon insertion.

According to one application of the present invention, control unit 16 is configured to apply a voltage between first electrode 12 and second electrode 14, and to configure the voltage to electroosmotically drive fluid from the site outside nucleus pulposus 62, into the nucleus pulposus. It is hypothesized that this driving of the fluid is beneficial for subjects suffering from intervertebral disc fluid loss, by generally treating and/or preventing further degeneration in disc 60. Alternatively or additionally, control unit 16 may be configured to configure the voltage to electroosmotically drive fluid from the nucleus pulposus, to the site outside the nucleus pulposus.

As described with reference to FIG. 1, for some applications, apparatus 10 is configured to detect a pressure at at least one of the electrodes (e.g., the pressure above atmospheric pressure, at the implantation site of the electrode), and to apply the treatment voltage in response to the detected pressure. As also described with reference to FIG. 1, for some applications, apparatus 10 is configured to detect a pressure difference between the implantation sites of the electrodes, and to apply the treatment voltage in response to the detected pressure difference. As further described with reference to FIG. 1, for some such applications, apparatus 10 is configured to detect the pressure difference by detecting a voltage, such as a streaming potential, between the electrodes, that is indicative of the pressure difference between the sites. When apparatus 10 is implanted as shown in FIG. 5, and is configured to drive fluid into the nucleus pulposus, the apparatus may thereby be configured to detect the pressure at nucleus pulposus 62 (e.g., the pressure above atmospheric pressure), and/or to detect the pressure difference and/or the voltage between the nucleus pulposus and the site outside of the nucleus pulposus, and to apply the treatment voltage if the detected pressure, pressure difference, and/or voltage is smaller than a threshold pressure, pressure difference, and/or voltage.

As described hereinabove, apparatus 10 may alternatively or additionally be configured to drive fluid out of the nucleus pulposus. For such applications, the apparatus may thereby be configured to detect the pressure at the nucleus pulposus (e.g., the pressure above atmospheric pressure), and/or to detect the pressure difference and/or the voltage between the nucleus pulposus and the site outside of the nucleus pulposus, and to apply the treatment voltage if the detected pressure, pressure difference, and/or voltage is greater than a threshold pressure, pressure difference, and/or voltage.

Typically, the detected voltage is detected while the treatment voltage is not applied. For example, control unit may be configured to apply the treatment voltage and detect the detected voltage in a sequence, and/or to periodically stop applying the treatment voltage so as to detect the detected voltage.

Figure 6:
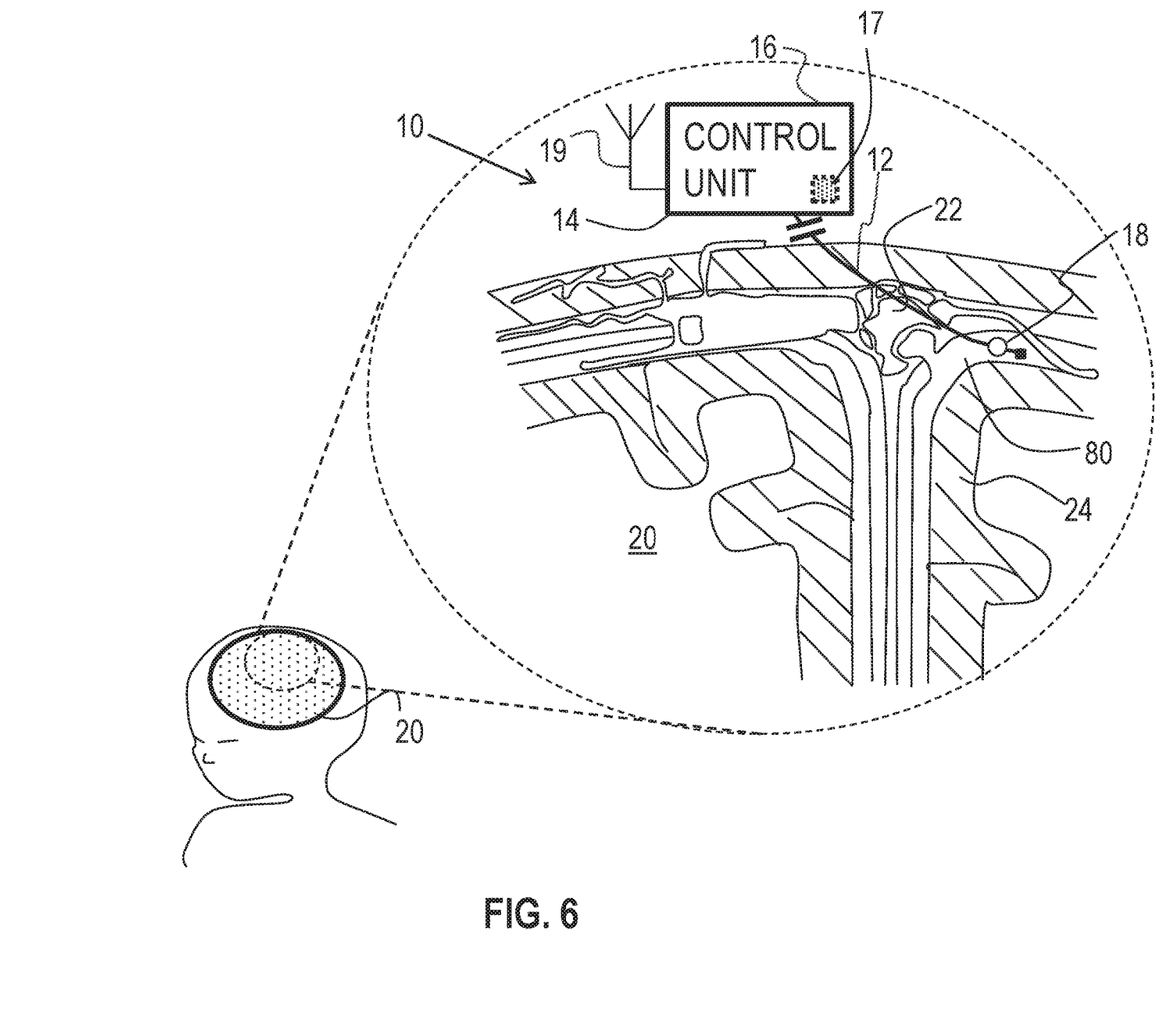
FIG. 6 is a schematic illustration of a system for altering throughput of fluid in the brain of a subject, in accordance with some applications of the invention.

Reference is made to FIG. 6 which is a schematic illustration of medical apparatus 10, comprising generally the same components as shown in FIG. 1, for driving fluid in brain 20 of a subject, in accordance with some applications of the invention. Typically, first electrode 12 is implanted in a subarachnoid cavity 80 of the brain of the subject, and second electrode 14 is implanted at a site outside of the subarachnoid cavity, such as outside of the brain of the subject. For example, and as shown in FIG. 6, second electrode 14 may be integral with control unit 16 (e.g., integral with a casing thereof), and control unit 16 may be subcutaneously implanted elsewhere in the body, such as at a site in the torso of the subject. For some applications, first electrode 12 is placed at a different site in the brain of the subject.

According to one application of the present invention, control unit 16 is configured to apply a voltage between first electrode 12 and second electrode 14, and to configure the voltage to electroosmotically drive fluid out of subarachnoid cavity 80. It is further hypothesized by the inventor that the driving of the fluid is beneficial for subjects suffering from and/or at risk of Alzheimer's disease (e.g., that are asymptomatic of Alzheimer's disease), by facilitation of clearance of substances, such as amyloid-beta and metal ions (e.g., iron and copper ions), from the brain of the subject. For example, reduction of the concentration of amyloid beta monomers and/or oligomers from the brain may (1) inhibit the formation and/or growth of amyloid-beta plaques in the brain, and/or (2) reduce direct toxic effects of the oligomers on neurons of the brain. It is also hypothesized that, for some applications, this driving of the fluid may be used to treat a subject suffering from normal pressure hydrocephalus.

It is further hypothesized by the inventor that the driving of the fluid reduces the volume of fluid in at least parts of the brain, such as within ventricles of the brain, suppressing enlargement of the ventricles, e.g., caused by fluid pressure in the ventricles.

As described with reference to FIG. 1, for some applications, apparatus 10 is configured to detect a pressure at at least one of the electrodes (e.g., the pressure above atmospheric pressure, at the implantation site of the electrode), and to apply the treatment voltage in response to the detected pressure. As also described with reference to FIG. 1, for some applications, apparatus 10 is configured to detect a pressure difference between the implantation sites of the electrodes, and to apply the treatment voltage in response to the detected pressure difference. As further described with reference to FIG. 1, for some such applications, apparatus 10 is configured to detect the pressure difference by detecting a voltage, such as a streaming potential, between the electrodes, that is indicative of the pressure difference between the sites. When apparatus 10 is implanted as shown in FIG. 6, the apparatus may thereby be configured to detect the pressure at subarachnoid cavity 80 (e.g., the pressure above atmospheric pressure), and/or to detect the pressure difference and/or the voltage between the subarachnoid cavity and the site outside of the subarachnoid cavity, and to apply the treatment voltage if the detected pressure, pressure difference, and/or voltage is greater than a threshold pressure, pressure difference, and/or voltage.

Typically, the detected voltage is detected while the treatment voltage is not applied. For example, control unit may be configured to apply the treatment voltage and detect the detected voltage in a sequence, and/or to periodically stop applying the treatment voltage so as to detect the detected voltage.

Figure 7:
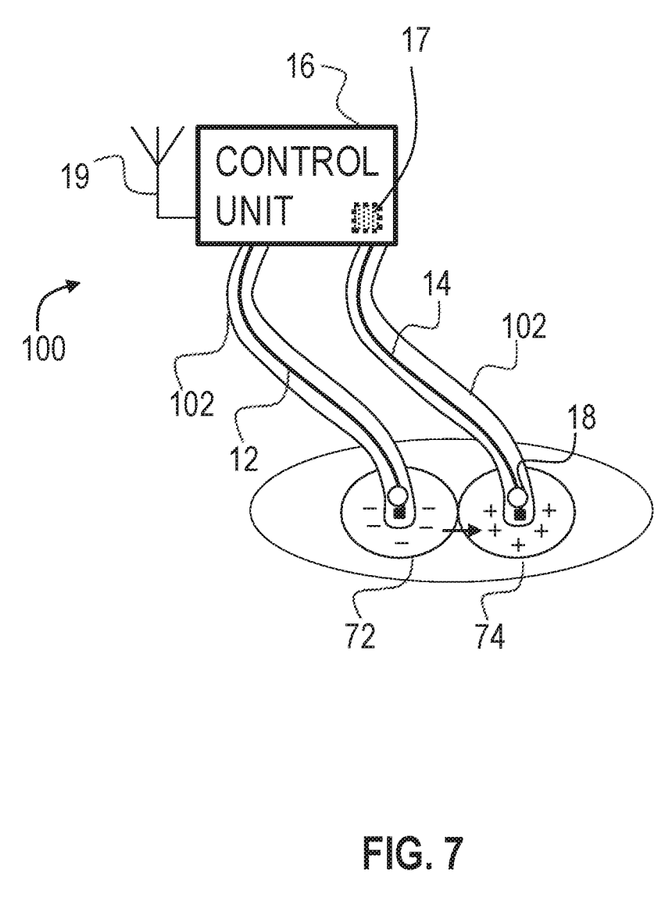
FIG. 7 is a schematic illustration of a system for applying a capacitance-based current, in accordance with some applications of the present invention.

Reference is now made to FIG. 7, which is a schematic illustration of medical apparatus 100, for applying a capacitance-based current to a subject, in accordance with some applications of the invention. Typically, apparatus 100 comprises apparatus 10 and/or components thereof but, in apparatus 100, first electrode 12 and second electrode 14 are insulated with an insulating material 102 (e.g., silicone). Typically, when control unit 16 applies a voltage between first electrode 12 and second electrode 14, a capacitance-based current flows from first electrode 12 to second electrode 14, resulting in fluid electroosmotically moving from a first site 72 in the body toward a second site in the body. For example, this technique may be practiced to electroosmotically drive fluid (e.g., to alter the throughput of fluid) between any of the sites described in FIGS. 1-6, mutatis mutandis. For some applications, insulating material 102 inhibits corrosion of electrodes 12 and/or 14. For some applications, only one of electrodes 12 and 14 is insulated with insulating material 102.

Reference is again made to FIGS. 1-7. For some applications (e.g., as described with reference to FIG. 5, mutatis mutandis), it may be desirable to increase the pressure difference between the implantation sites of electrodes 12 and 14. For some such applications, the apparatus is thereby configured to detect the pressure (e.g., the pressure above atmospheric pressure), and/or to detect the pressure difference and/or the voltage between the implantation sites, and to apply the treatment voltage if the detected pressure, pressure difference, and/or voltage is smaller than a threshold pressure, pressure difference, and/or voltage.

Reference is again made to FIGS. 1-7. For some applications, electrode 12 and/or electrode 14 comprise more than one electrode, respectively, e.g., so as to distribute the treatment voltage over a larger region of a tissue compared to a single electrode. For example, with respect to the configuration shown in FIG. 1, a plurality of electrodes 14 may be implanted in cerebral cortex 24, each of the electrodes 14 being implanted at a different region of the cerebral cortex, so as to drive fluid from each of the regions of the cerebral cortex toward superior sagittal sinus 22. Similarly, for some applications, electrode 12 and/or electrode 14 may comprise a large (e.g., elongate, planar, and/or a mesh) electrode that is thereby configured to distribute the treatment voltage over a larger region of tissue compared to a smaller electrode.

Reference is again made to FIGS. 1-6. It is to be noted that FIGS. 1-6 show examples of anatomical sites in which apparatus 10 may be used, and that apparatus 10 may be used in anatomical sites (e.g., other anatomical sites) that include a native membrane across which a pressure difference exists.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
    implanting a first electrode at a first site in a cerebral cortex of a brain of a subject suffering from hydrocephalus;
    implanting a second electrode at a second site in a superior sagittal sinus of the subject; and
    treating the hydrocephalus by electroosmotically driving fluid from the cerebral cortex to the superior sagittal sinus, by applying a treatment voltage between the first and the second electrodes.

2. The method according to claim 1,
    wherein the hydrocephalus is normal pressure hydrocephalus,
    wherein implanting the first and the second electrodes comprises implanting the first and the second electrodes in the subject suffering from normal pressure hydrocephalus, and
    wherein treating the hydrocephalus comprises treating the normal pressure hydrocephalus by electroosmotically driving the fluid out of the first site.

3. The method according to claim 1, wherein applying the treatment voltage comprises applying the treatment voltage as direct current.

4. The method according to claim 1, further comprising providing a rest period during which the treatment voltage is not applied, and applying, during the rest period, an opposite voltage between the first and the second electrodes, the opposite voltage being opposite to the treatment voltage and having a lower magnitude than the treatment voltage.

5. The method according to claim 1, wherein applying the treatment voltage comprises applying a capacitative current.

6. The method according to claim 1, further comprising detecting a pressure difference between the first and the second sites, wherein applying the treatment voltage comprises applying the treatment voltage in response to the detected pressure difference.

7. The method according to claim 6, wherein detecting the pressure difference comprises detecting a voltage between the first and the second sites, and wherein applying the treatment voltage comprises applying the treatment voltage in response to the detected voltage.

8. The method according to claim 7, wherein detecting the detected voltage comprises detecting a streaming potential.

9. The method according to claim 7, wherein detecting the voltage between the first and the second sites comprises detecting a voltage between the first and second electrodes.

10. A method comprising:
   implanting a first electrode at a first site within a subarachnoid cavity of a brain of a subject suffering from hydrocephalus; implanting a second electrode at a second subcutaneous site of the subject outside the brain, and
   treating the hydrocephalus by electroosmotically driving fluid out of the subarachnoid cavity, by applying a treatment voltage between the first and the second electrodes.

11. The method according to claim 10,
   wherein the second electrode is integral with a casing of a control unit, and
   wherein implanting the second electrode comprises subcutaneously implanting the casing of the control unit.

12. The method according to claim 10,
   wherein the hydrocephalus is normal pressure hydrocephalus,
   wherein implanting the first and the second electrodes comprises implanting the first and the second electrodes in the subject suffering from normal pressure hydrocephalus, and
   wherein treating the hydrocephalus comprises treating the normal pressure hydrocephalus by electroosmotically driving the fluid out of the first site.

13. The method according to claim 10, wherein applying the treatment voltage comprises applying the treatment voltage as direct current.

14. The method according to claim 10, further comprising providing a rest period during which the treatment voltage is not applied, and applying, during the rest period, an opposite voltage between the first and the second electrodes, the opposite voltage being opposite to the treatment voltage and having a lower magnitude than the treatment voltage.

15. The method according to claim 10, wherein applying the treatment voltage comprises applying a capacitative current.

16. The method according to claim 10, further comprising detecting a pressure difference between the first and the second sites, wherein applying the treatment voltage comprises applying the treatment voltage in response to the detected pressure difference.

17. The method according to claim 16, wherein detecting the pressure difference comprises detecting a voltage between the first and the second sites, and wherein applying the treatment voltage comprises applying the treatment voltage in response to the detected voltage.

18. The method according to claim 17, wherein detecting the detected voltage comprises detecting a streaming potential.

19. The method according to claim 17, wherein detecting the voltage between the first and the second sites comprises detecting a voltage between the first and second electrodes.

* * * * *